US012667428B2

(12) United States Patent   (10) Patent No.: US 12,667,428 B2
Birkhold et al.   (45) Date of Patent: Jun. 30, 2026

(54) VISUAL SUPPORT FOR SPINAL CURVATURE THERAPY

(71) Applicant: Siemens Healthineers AG, Forchheim (DE)

(72) Inventors: Annette Birkhold, Stuttgart (DE); Karthik Shetty, Erlangen (DE)

(73) Assignee: Siemens Healthineers AG, Forchheim (DE)

( * ) Notice: Subject to any disclaimer, the term of this patent is extended or adjusted under 35 U.S.C. 154(b) by 287 days.

(21) Appl. No.: 18/610,864

(22) Filed: Mar. 20, 2024

(65) Prior Publication Data

US 2024/0315780 A1   Sep. 26, 2024

(30) Foreign Application Priority Data

Mar. 20, 2023   (DE) ...................... 10 2023 202 423.3

(51) Int. Cl.
*A61B 34/20*   (2016.01)
*G06T 7/00*   (2017.01)

(52) U.S. Cl.
CPC ............ *A61B 34/20* (2016.02); *G06T 7/0012* (2013.01); *A61B 2034/2059* (2016.02); *G06T 2207/30012* (2013.01)

(58) Field of Classification Search
CPC . G06T 2207/30012; G06T 2207/20116; G06T 2207/30204; G06T 7/0012;
(Continued)

(56) References Cited

U.S. PATENT DOCUMENTS

2008/0044074 A1* 2/2008 Jerebko ...................... G06T 7/12
382/128
2014/0323845 A1* 10/2014 Forsberg ................... G06T 7/60
600/407
(Continued)

FOREIGN PATENT DOCUMENTS

DE   102021210991 A1   3/2023

OTHER PUBLICATIONS

A. Gebhard, et al., "A Practical Guide to Statistical Shape Models Featuring Hands-on Examples in CONRAD," Pattern Recognitions Lab; FAU; MICCAI 2018 Educational Challenge, 2018, pp. 1-28.
(Continued)

*Primary Examiner* — Alex Kok S Liew
(74) *Attorney, Agent, or Firm* — Lempia Summerfield Katz LLC

(57)   ABSTRACT

A patient model for mapping a set of pose parameters and a set of shape parameters onto a surface grid is provided. Patient image data that represents a spine of a patient is provided, and a patient-specific set of pose parameters and a patient-specific set of shape parameters are determined based on the patient image data. An initial surface grid that represents the spine in an initial state with spine curvature is calculated. The calculation includes applying the patient model to the patient-specific set of pose parameters and the patient-specific set of shape parameters. A target surface grid that represents the spine of the patient in a target state with a straightened spine is provided. By comparing the target surface grid with the initial surface grid, a displacement field for the spine is determined and, depending on the displacement field, support information is generated and displayed visually.

18 Claims, 3 Drawing Sheets

(58) Field of Classification Search
    CPC .......... G06T 17/20; G06T 2207/10016; G06T
                2207/10088; G06T 2207/20101; G06T
                2207/20124; G06T 2207/20168; G06T
                2207/30096; G06T 2207/30196; G06T
                7/12; G06T 7/149; G06T 7/246; G06T
                2207/10116; G06T 2207/10132; G06T
            7/337; G06T 7/74; A61B 17/7011; A61B
                2034/102; A61B 34/10; A61B 5/0064;
                A61B 17/7014; A61B 17/7019; A61B
                2017/00407; A61B 2034/108; A61B
                2090/376; A61B 34/20; A61B 5/0035;
                A61B 5/053; A61B 5/282; A61B 5/296;
                            A61B 5/6804; A61B 5/6823
    See application file for complete search history.

(56)                 References Cited

U.S. PATENT DOCUMENTS

2015/0313566 A1*  11/2015  Diers ..................... A61B 6/505
                                                              378/63
2022/0296143 A1*   9/2022  Ishida ................... G16H 30/20

OTHER PUBLICATIONS

Anguelov et al., "SCAPE: Shape Completion and Animation of
People," ACM transactions on graphics (TOG), vol. 24, No. 3, 2005,
pp. 408-416.

Aubert, Benjamin, et al. "Toward automated 3D spine reconstruc-
tion from biplanar radiographs using CNN for statistical spine
model fitting," IEEE transactions on medical imaging 38.12 (2019),
pp. 2796-2806.
Harrison Farber, S., et al., "Radiation exposure to the surgeon
during minimally invasive spine procedures is directly estimated by
patient dose," European Spine Journal 27 (2018), pp. 1911-1917.
Guan, Peng et al.: "Estimating Human Shape and Pose from a
Single Image," IEEE 12th International Conference on Computer
Vision; 2009, pp. 1381-1388.
Kanazawa, Angjoo, et al., "End-to-end recovery of human shape
and pose," Proceedings of the IEEE conference on computer vision
and pattern recognition. 2018, pp. 7122-7131.
Loper M. et al.: "SMPL: A Skinned Multi-Person Linear Model,"
ACM transactions on graphics (TOG) 34.6 (2015), pp. 1-16.
Kolotouros, Nikos, et al., "Learning to reconstruct 3D human pose
and shape via model-fitting in the loop," Proceedings of the IEEE/
CVF international conference on computer vision. 2019, pp. 2252-
2261.
Shetty, Karthik, et al. "BOSS: Bones, organs and skin shape model,"
Computers in Biology and Medicine 165 (2023), pp. 1-13.
Smedema, Jette. "Rod bending accuracy improvement for spinal
fusion in adolescent idiopathic scoliosis patients: An exploratory
finite element analysis," (2022), pp. 1-142.
Tan, Jiong Hao, and Hee-Kit Wong, "Minimally invasive options in
adolescent idiopathic scoliosis," Indian Spine Journal 3.2 (2020),
pp. 207-215.
Wikipedia "Iterative Closest Point Algorithm"; Obtained: Mar. 16,
2021, with translation, pp. 1-5.

* cited by examiner

VISUAL SUPPORT FOR SPINAL CURVATURE THERAPY

This application claims the benefit of German Patent Application No. DE 10 2023 202 423.3, filed on Mar. 20, 2023, which is hereby incorporated by reference in its entirety.

BACKGROUND

Pathological curvature of the spine (e.g., scoliosis) may be treated, for example, by spinal fusion, vertebral body tethering, or an internal fusion system under X-ray monitoring (e.g., fluorescence-assisted).

For example, due to the significant vertebral rotations in such conditions, it may be difficult to determine the ideal trajectory of pedicle screws, especially if there is insufficient visibility of anatomical orientation points. The resulting need for repeated fluoroscopy leads to increased radiation exposure for medical personnel and patients. In addition, the presence of a rigid curvature, vertebral rotation, limited visibility, and soft tissue may complicate contoured rod passage and reposition maneuvers.

It is therefore desirable to be able to provide medical personnel with further assistance during the treatment.

It is known for modeling complex bodies (e.g., human bodies) to use statistical models in which training data is determined from a specific population of individuals characterized, for example, by a certain age, sex, height and/or body weight, and so on (e.g., in the form of camera images, X-ray projection images, or computed tomography reconstructions). This training data may then be used to determine a correlation between specific parameters and three-dimensional surface grids (e.g., triangular grids). Such a surface grid is also referred to as a mesh and approximately represents a body surface or, depending on the type of training data, also internal organs and/or skeletal structures.

Usually, a set of shape parameters is used for parameterization, which describes how the shape of the surface grid deviates from a reference shape or average shape of a template of the model, as well as a set of pose parameters, which describes how the individual components of the surface grid (e.g., body parts or organs or parts thereof) are twisted and/or displaced in relation to a reference pose. The models may be deformable (e.g., surface grids may be transformed into other surface grids with other pose parameters and/or shape parameters using a process known as skinning).

In the publication M. Loper et al: "SMPL: A Skinned Multi-Person Linear Model," ACM Transactions on Graphics 2015, a body shape and pose model known as a skinned multi-person linear model, SMPL, is described.

The article A. Gebhard et al: "A Practical Guide to Statistical Shape Models Featuring Hands-on Examples in CONRAD," MICCAI 2018 Educational Challenge, describes the basics of statistical shape modeling (SSM).

The publication A. Kanazawa et al: "End-to-end Recovery of Human Shape and Pose," arXiv: 171206584v2, describes Human Mesh Recovery, HMR, an end-to-end approach for reconstructing a complete 3D mesh of a human body from a single RGB image using a neural network. For example, a set of pose parameters and a set of shape parameters are generated from an image and the 3D mesh is generated based on these.

The publication N. Kolotouros et al: "Learning to Reconstruct 3D Human Pose and Shape via Model-fitting in the Loop," arXiv: 1909.12828v1 describes methods for model-based estimation of human posture. The publication combines optimization-based methods that iteratively fit a parametric body model to 2D observations with regression-based methods that use a deep neural network in order to estimate the model parameters directly from the pixels.

The publication D. Anguelov et al: "SCAPE: shape completion and animation of people," ACM Transactions on Graphics, 24, 3, 408-416 describes SCAPE, a data-driven method for creating a human shape model that covers variations in shape and pose. The method is based on a representation that considers both articulated and non-rigid deformations.

The publication P. Guan et al: "Estimating Human Shape and Pose from a Single Image" Int. Conf. on Computer Vision, ICCV 2009, 1381-1388 describes a method for pose and shape estimation of humans based on two-dimensional images based on SCAPE.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a possibility for the improved visual support for spinal curvature therapy is provided.

The present embodiments are based on the idea of using a patient model to generate a three-dimensional surface grid that represents the spine and internal organs in order to calculate an initial surface grid that is based on patient image data and represents an initial state with the spinal curvature. This is compared with a target surface grid that represents a target state with a straightened spine, and a displacement field for the vertebrae of the spine is calculated based on the comparison. The displacement field may be used to support the therapy.

According to one aspect of the present embodiments, a method for visually supporting a therapy of a spinal curvature of a patient is disclosed. The following acts are performed (e.g., using at least one computing unit). A patient model for a predetermined patient population is provided, where the patient model is suitable for mapping a set of pose parameters and a set of shape parameters onto a three-dimensional surface grid that represents at least a spine and internal organs of the patient population. Patient image data that shows at least a spine and internal organs of the patient is provided. Based on the patient image data, a patient-specific set of pose parameters and a patient-specific set of shape parameters are determined.

An initial surface grid that represents at least the spine and internal organs of the patient in an initial state with the spinal curvature is calculated. The calculation of the initial surface grid involves applying the patient model to the patient-specific set of pose parameters and the patient-specific set of shape parameters. A target surface grid that represents at least the spine and internal organs of the patient in a target state with a straightened spine is provided.

By comparing the target surface grid with the initial surface grid, a displacement field is determined for a plurality of vertebrae of the spine of the patient. Depending on the displacement field, support information for the visual support for spinal curvature therapy is generated and visually displayed (e.g., on a display device).

Unless otherwise specified, all acts of the method may be performed by a data processing facility that has at least one computing unit. For example, the at least one computing unit is configured or adapted to perform the acts of the method. For this purpose, the at least one computing unit may, for example, store a computer program that includes commands that, when executed by the at least one computing unit, cause the at least one computing unit to execute the method.

The patient model may be understood as a mapping M that maps a given set of pose parameters and a given set of shape parameters onto a three-dimensional surface grid (e.g., to an ordered set of points in three-dimensional space that correspond to vertices of the surface grid).

$$M: \mathbb{R}^{K \times L} \rightarrow \mathbb{R}^{3N}, (\theta, \beta) \longmapsto M(\theta, \beta).$$

In this case, K is the number of pose parameters in the set of pose parameters, K is the number of shape parameters in the set of shape parameters, and N is the number of vertices of the surface grid.

The surface grid represents at least the spine and internal organs of the patient population, for example, by approximating the surfaces of the spine (e.g., the vertebral bodies) and the internal organs (e.g., their position, orientation and shape, as the internal organs are found on average in the patient population). Accordingly, the surface grid does not necessarily represent the spine and internal organs of an actual individual of the patient population.

For example, the surface grid may represent corresponding surfaces of a majority of all internal organs or all internal organs and, in addition to the spine, a majority of all bones or all bones. The surface grid may also represent, for example, a part of the skin surface or the entire skin surface.

As described in the publications mentioned in the introduction, the patient model may be constructed using camera images, X-ray projection images, and/or three-dimensional computed tomography reconstructions (e.g., whole-body CT reconstructions).

The patient model is, for example, a body shape and body pose model (e.g., a skinned multi-person linear model, SMPL, as mentioned above, or a body shape and body pose model based on it).

For example, the patient image data depicts the initial state in which the spinal curvature is present. The patient image data includes, for example, one or more X-ray projection images (e.g., two or more X-ray projection images with different recording perspectives) and/or one or more three-dimensional CT reconstructions of the individual patient having a spinal curvature that is to be treated. The patient image data may also include image data of the patient that is generated by other imaging modalities, such as PET-CT or MRT (MRI). The X-ray projection images and/or CT reconstructions and/or other image data depict the spine and at least some of the internal organs of the patient.

The patient-specific shape and pose parameters for the individual patient may therefore be determined from the patient image data. By applying the patient model to the patient-specific set of pose parameters and the patient-specific set of shape parameters, the initial surface grid may therefore be calculated. Alternatively, a preliminary surface grid may be calculated by applying the patient model to the patient-specific set of pose parameters, and the patient-specific set of shape parameters and the initial surface grid may be calculated based on the preliminary surface grid (e.g., by making detailed adjustments to the patient image data, such as using a registration method, such as a method for non-rigid registration).

The target surface grid differs from the initial surface grid, for example, in that the spine is straightened in the target state. The target surface grid or the target state therefore represents a therapeutic goal, for example.

The target surface grid may be generated in various ways. For example, the initial surface grid may be manually modified to straighten the spines. It is also possible to use respective predetermined reference sets of pose parameters and/or shape parameters and apply the patient model to the respective predetermined reference sets of pose parameters and/or shape parameters in order to calculate the target surface grid. Optimization methods may also be performed in order to deform the initial surface grid under predetermined boundary conditions in order to calculate the target surface grid.

The comparison of the target surface grid with the initial surface grid may include, for example, comparing the positions of all vertices of the target surface grid or a part thereof with the positions of the corresponding vertices of the initial surface grid (e.g., calculating the respective magnitude and/or the respective direction of a corresponding vector that connects a vertex of the target surface grid to a corresponding vertex of the source surface grid).

The displacement field corresponds, for example, to a vector field of the vectors that connect vertices of the target surface grid to corresponding vertices of the initial surface grid, at least for parts of the target surface grid and the initial surface grid that represent the vertebrae of the spine. The displacement field may also correspond to a scalar field of the amounts of these vectors.

The displacement field therefore indicates the magnitude and, if necessary, the direction of a displacement by which the individual vertebrae of the spine should be displaced for the spinal curvature therapy in order to at least approximately achieve the target state.

In order to support the therapy, the support information that is dependent on the displacement field is displayed visually.

The support information includes, for example, a visual representation of the displacement field or a variable derived from the displacement field. In this manner, medical personnel may thus be shown visually which vertebrae should still be displaced and by how much and/or in which direction in order to at least approximately achieve the target state, and/or how large the deviation of the position and/or orientation of the vertebrae from the target state still is.

In various embodiments, updated patient image data may also be generated and provided during the therapy (e.g., by an X-ray imaging modality, a CT imaging modality, and/or another imaging modality). The acts of the method according to the present embodiments for calculating the initial surface grid, determining the displacement field, generating and displaying the support information, and, depending on the embodiment, possibly generating the target surface grid if this was based on the patient image data, may then be repeated using the updated patient image data in lieu of the patient image data. In this manner, the medical personnel may be optimally supported during the entire therapy.

According to at least one embodiment of the method, the support information includes a magnitude of the displacement field (e.g., as a function of the location).

The visual representation of the magnitude of the displacement field may, for example, be a color-coded or greyscale-coded representation of the magnitude of the displacement field. The visual representation of the magnitude of the displacement field may, for example, be superimposed on the patient image data or part of the patient image data or display image data derived from the patient image data, and the superimposition may then be displayed visually.

According to at least one embodiment of the method, the support information includes a direction of the displacement field (e.g., as a function of the location).

The visual representation of the direction of the displacement field may, for example, include arrows or the like that indicate the respective direction. The visual representation of the direction of the displacement field may, for example, be superimposed on the patient image data or part of the patient image data or display image data derived from the patient image data, and the superimposition may then be displayed visually.

According to at least one embodiment of the method, a trained artificial neural network is applied to the patient image data so as to determine the patient-specific set of pose parameters and the patient-specific set of shape parameters.

The neural network may be configured according to HMR, for example. The architecture and training of the neural network may be based, for example, on the aforementioned publication by Kanazawa et al.

This allows the patient-specific set of pose parameters and the patient-specific set of shape parameters to be determined in a simple manner and with a high degree of accuracy.

According to at least one embodiment, at least one feature map is generated so as to determine the patient-specific set of pose parameters and the patient-specific set of shape parameters by applying a feature encoder module of the neural network to the patient image data. The patient-specific set of pose parameters and the patient-specific set of shape parameters are generated by applying an iterative regression module of the neural network to the at least one feature map.

According to at least one embodiment, the target surface grid is calculated by applying the patient model to a predetermined reference set of pose parameters and the patient-specific set of shape parameters.

In other words, the target surface grid and the initial surface grid differ from each other in that the reference set of pose parameters is used to calculate the target surface grid, whereas the patient-specific set of pose parameters is used to calculate the initial surface grid. In both cases, the patient-specific set of shape parameters is also used.

The reference set of pose parameters may also be referred to as the resting pose or zero pose. For example, the reference set of pose parameters describes the average pose of the patient model or template and may be taken, for example, from the patient model provided. The resting pose may be adjusted or set manually when the patient model is generated or may be determined as part of the training of the patient model.

In such embodiments, the target surface grid may be generated with particularly low computational effort and therefore quickly. Such embodiments are particularly advantageous if the initial surface grid is generated directly by applying the patient model to the patient-specific set of pose parameters and the patient-specific set of shape parameters (e.g., without using a non-rigid registration).

According to at least one embodiment, the patient image data includes two or more X-ray projection images with different recording directions (e.g., X-ray projection images that map the spine and the internal organs of the patient from different viewing directions). For example, the two or more X-ray projection images are generated in a method act of the method according to the present embodiments using an X-ray imaging modality.

Due to the different recording directions, the patient image data as a whole implicitly includes depth information, so that the patient-specific set of pose parameters and the patient-specific set of shape parameters may be determined with greater accuracy.

In embodiments in which the neural network is used to determine the patient-specific set of pose parameters and the patient-specific set of shape parameters, the two or more X-ray projection images may, for example, be fused, and the fused X-ray projection images may be fed to the neural network (e.g., to the feature encoder module). Alternatively, the two or more X-ray projection images may be fed to the feature encoder module or respectively to one of two or more feature encoder modules, and the resulting feature maps may be fused. The fused feature maps may then be fed to the iterative regression module.

According to at least one embodiment, the patient image data includes a three-dimensional computed tomography reconstruction, CT reconstruction (e.g., a cone beam computed tomography reconstruction, CBCT reconstruction). For example, the CT reconstruction is generated in a method act of the method according to the present embodiments using a CT imaging modality.

This allows the spine and internal organs to be mapped with greater accuracy, which also results in more accurate patient-specific pose parameters and shape parameters.

According to at least one embodiment, a preliminary surface grid is calculated by applying the patient model to the patient-specific set of pose parameters and the patient-specific set of shape parameters. The initial surface grid is generated by performing at least one non-rigid registration depending on the preliminary surface grid and the patient image data.

Such embodiments are particularly advantageous when the patient image data includes the CT reconstruction. For example, the CT reconstruction may be segmented by applying a known segmentation algorithm, and the preliminary surface grid may be adapted to the CT reconstruction at least by non-rigid registration in order to obtain a particularly accurate initial surface grid.

The fact that at least one non-rigid registration is performed may be understood, for example, such that further acts for adapting the preliminary surface grid to the patient image data may optionally also be performed (e.g., before and/or after the non-rigid registration).

The non-rigid registration may include, for example, minimizing a deviation of the preliminary surface grid from the patient image data and/or applying an iterative closest point, ICP, algorithm.

In various embodiments (e.g., in embodiments in which the non-rigid registration is performed), an optimization process is performed so as to generate the target surface grid based on the initial surface grid, by which a deviation between a set of pose parameters according to the target surface grid and the reference set of pose parameters is minimized.

As a result, the target surface grid may be generated more realistically overall. For example, anatomical boundary conditions may be taken into account during optimization (e.g., a distance between the bone and a skin surface that is as constant as possible).

According to at least one embodiment, a digitally reconstructed X-ray image, DRR, is generated based on the target surface grid, and the support information includes the DRR.

The DRR may, for example, be displayed on the display device and/or another display device as an alternative to or in addition to the visual representation of the displacement field.

According to a further aspect of the present embodiments, a data processing apparatus is provided. The data processing apparatus has at least one computing unit that is configured so as to perform a method according to the present embodiments.

For example, a computing unit may be understood to be a data processing device that includes a processing circuit. The computing unit may therefore, for example, process data so as to perform computing operations. This may also include operations to perform indexed accesses to a data structure (e.g., a look-up table, LUT).

For example, the computing unit may include one or more computers, one or more microcontrollers, and/or one or more integrated circuits (e.g., one or more application-specific integrated circuits, ASICs, one or more field-programmable gate arrays, FPGAs, and/or one or more systems on a chip, SoCs). The computing unit may also include one or more processors (e.g., one or more microprocessors, one or more central processing units, CPUs, one or more graphics processing units, GPUs, and/or one or more signal processors, such as one or more digital signal processors, DSPs). The computing unit may also include a physical or virtual network of computers or other mentioned units.

In various embodiments, the computing unit includes one or more hardware and/or software interfaces and/or one or more memory units.

A memory unit may be configured as a volatile data memory (e.g., as a dynamic random access memory, DRAM, or as a static random access memory, SRAM, or as a non-volatile data memory, such as a read-only memory, ROM, as a programmable read-only memory, PROM, as an erasable programmable read-only memory, EPROM, as a programmable read-only memory, EEPROM, as an electrically erasable programmable read-only memory, as a flash memory or a flash, EEPROM, as a ferroelectric random access memory, FRAM, as a magneto resistive random access memory, MRAM, or as a phase-change random access memory, PCRAM).

According to at least one embodiment of the data processing apparatus, this includes a display device, and the at least one computing unit is configured so as to display the support information on the display device.

According to a further aspect of the present embodiments, an apparatus for visually supporting a therapy of a spinal curvature of a patient is disclosed. In one embodiment, the apparatus includes a data processing apparatus according to the present embodiments that includes the display device. The apparatus has an imaging modality for generating the patient image data. The at least one computing unit is configured so as to display the support information on the display device.

The imaging modality is, for example, an X-ray imaging modality or a CT imaging modality.

Further embodiments of the apparatus according to the present embodiments for the visual support for spinal curvature therapy follow directly from the various embodiments of the method according to the present embodiments and conversely. For example, individual features and corresponding explanations as well as advantages relating to the various embodiments of the method according to the invention may be transferred analogously to corresponding embodiments of the apparatus according to the present embodiments. For example, the apparatus according to the present embodiments is configured or programmed to perform a method according to the present embodiments. For example, the apparatus according to the present embodiments performs the method according to the present embodiments.

According to a further aspect of the present embodiments, a computer program including commands is provided. When the commands are executed by a data processing apparatus (e.g., the at least one computing unit of a data processing device apparatus according to the present embodiments), the commands cause the data processing apparatus to perform a method according to the present embodiments.

The commands may, for example, be in the form of program code. The program code may, for example, be provided as binary code or assembler and/or as source code of a programming language (e.g., C) and/or as a program script (e.g., Python).

According to a further aspect of the present embodiments, a computer-readable storage medium that stores a computer program according to the present embodiments is provided.

The computer program according to the present embodiments and the computer-readable storage medium according to the present embodiments may be understood as respective computer program products with the commands.

Further features of the present embodiments are disclosed in the claims, the figures, and the description of the figures. The features and feature combinations mentioned above in the description and the features and feature combinations mentioned below in the description of the figures and/or illustrated in the figures cannot only be used in the respectively mentioned combination but rather may also be used in other combinations of the present embodiments. For example, the present embodiments may also include embodiments and combinations of features that do not have all the features of an originally formulated claim. In addition, the present embodiments may include embodiments and combinations of features that go beyond or deviate from the combinations of features set out in the references of the claims.

The invention is explained in more detail below with reference to specific embodiments and associated schematic drawings. In the figures, same or functionally same elements may be provided with the same reference characters. The description of identical or functionally identical elements may not necessarily be repeated with respect to different figures.

DETAILED DESCRIPTION

Figure 1:
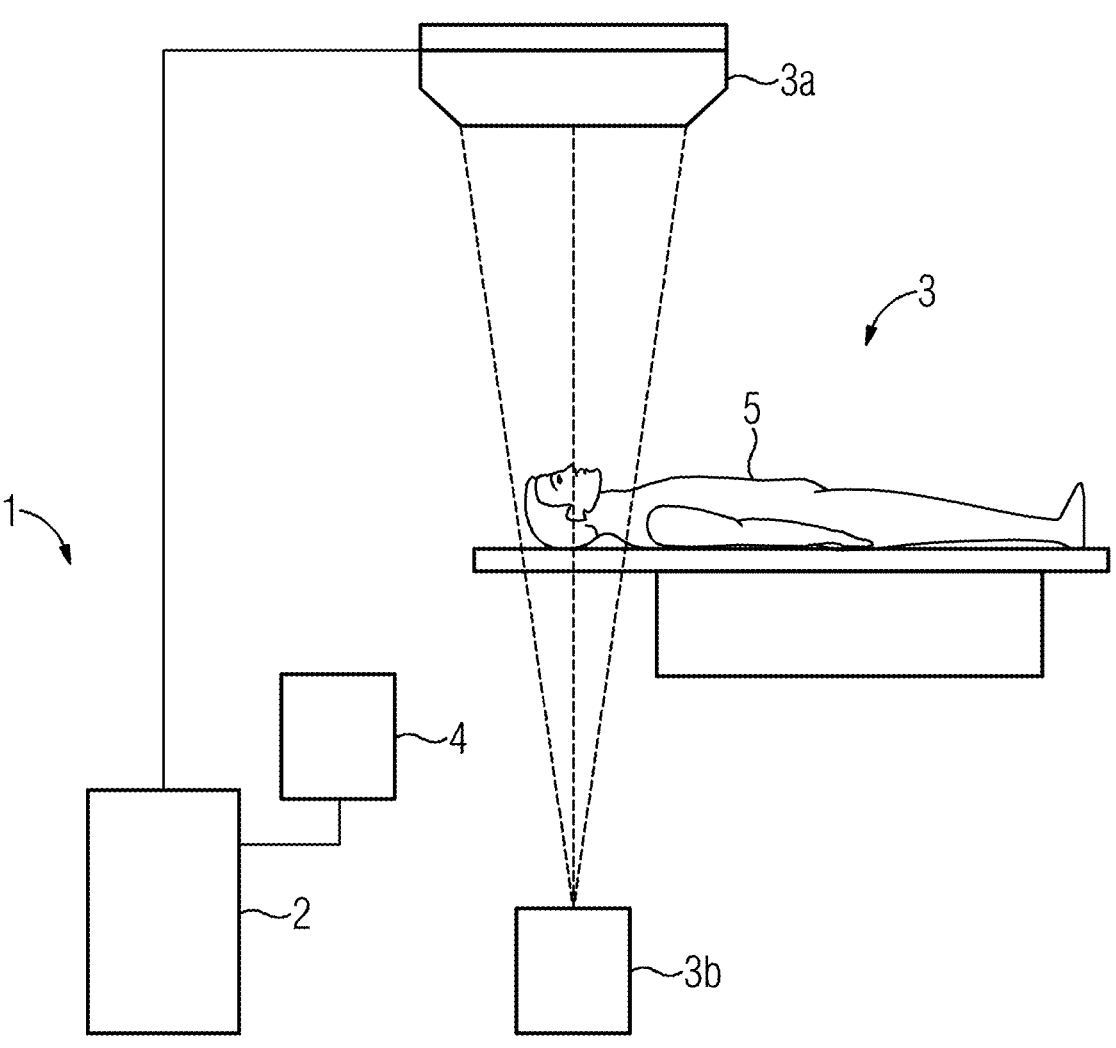
FIG. 1 shows a schematic representation of an example embodiment of an apparatus for visual support for spinal curvature therapy of a patient.

FIG. 1 schematically shows an example embodiment of an apparatus 1 for visual support for spinal curvature therapy of a patient 5.

The apparatus 1 has a data processing apparatus having at least one computing unit that in FIG. 1 and below is shown or referred to in simplified form as a single computing unit 2. The apparatus has an imaging modality 3 for generating patient image data 7 (cf., FIG. 2). For example, the imaging modality 3 is configured as an X-ray imaging modality or CT imaging modality. For example, the imaging modality 3 then has an X-ray source 3b and an X-ray detector 3a.

The X-ray detector 3a is configured so as to generate sensor data based on portions of X-rays emitted by the X-ray source 3b that pass through the patient 5. The computing unit 2 may, for example, generate one or more X-ray projection images based on the sensor data and, in the case of a CT imaging modality, generate a three-dimensional CT reconstruction from the X-ray projection images.

The apparatus 1 has a display device 4 on which the computing unit 2 may display support information 12, 13 (see FIG. 2) to medical personnel for the visual support for spinal curvature therapy.

The support information 12, 13 may be generated by the apparatus using a method according to the present embodiments.

Figure 2:
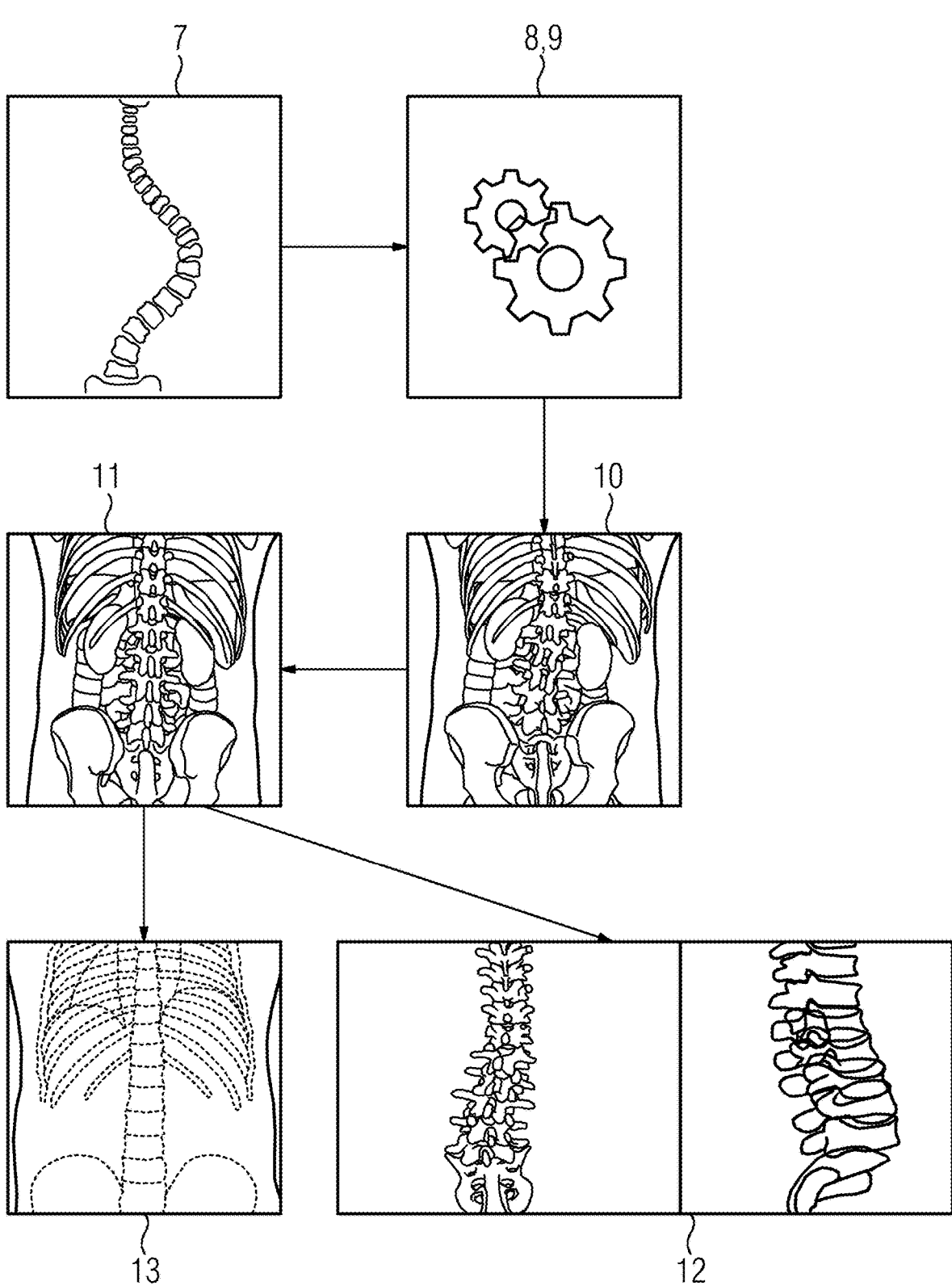
FIG. 2 shows a schematic flow diagram of an example embodiment of a method for the visual support for spinal curvature therapy of a patient.

FIG. 2 schematically shows a flow diagram of an example embodiment of a method.

In so doing, a patient model for a predetermined patient population is provided for mapping a set of pose parameters and a set of shape parameters onto a three-dimensional surface grid that represents at least a spine and internal organs of the patient population.

For example, the patient model is a statistical shape intensity patient model, SSIPM, and may also include, for example, implants or other devices. In some embodiments, the patient model may also include intensity distributions for each organ.

The patient image data 7 is generated and provided using the imaging modality. The patient image data 7 represents at least a spine and internal organs of the patient 5. Depending on the embodiment, the patient image data may include, for example, two or more two-dimensional X-ray projection images, a preoperative CT reconstruction, a CBCT recording, or a combination thereof. Based on the patient image data, the computing unit 2 determines a patient-specific set of pose parameters 8 and a patient-specific set of shape parameters 9.

Figure 3:
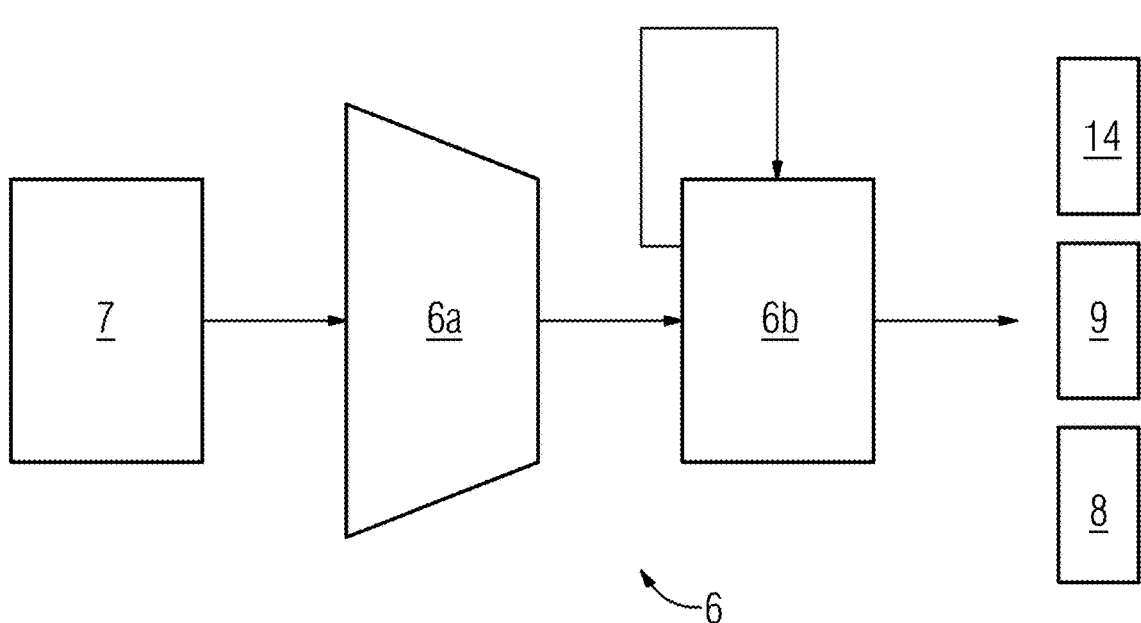
FIG. 3 shows a schematic block diagram of a neural network in a further example embodiment of a method for the visual support for spinal curvature therapy of a patient.

For this purpose, the computing unit 2 may, for example, apply a trained neural network 6 to the patient image data 7, as shown schematically in FIG. 3. For example, at least one feature map is generated by applying a feature encoder module 6a of the neural network 6 to the patient image data 7. The patient-specific set of pose parameters 8 and the patient-specific set of shape parameters 9 are generated by applying an iterative regression module 6b of the neural network 6 to the at least one feature map.

The neural network 6 may, for example, be based on HMR. The basic idea is based on HMR from the publication by Kanazawa et al. mentioned in the introduction, where the shape parameters 9, the pose parameters 8, and virtual camera parameters 14 for a statistical shape model are determined directly from images by the neural network 6 per regression. This may be done, for example, by the additional regression of specific 2D key points. Using the 2D key points on the image plane and 3D key points obtained by deforming the surface grid based on shape parameters 9 and pose parameters 8, perspective transformations for known camera parameters may then be used to accurately align the surface grid in three dimensions.

The extension to a number of (e.g., several) images (e.g., X-ray projection images or images from CT reconstructions) may be performed by training the feature encoder module 6a as a common feature encoder module 6a for multiple images. The same principle of perspective transformation may then be applied to the entire image set in order to determine the shape parameters 9 and pose parameters 8 and thus the surface grid in three dimensions.

Training data sets may be used to train the neural network 6, and each training data set includes X-ray projection images or DRRs from CT reconstructions and associated surface grids. To improve training, techniques using model-fitting-in-the-loop may be used, such as in the aforementioned publication by Kolotouros et al.

If the patient image data 7 includes a CT reconstruction, the bones and organs may be segmented based on this (e.g., by using a known additional neural network for segmentation). The surface grid may then be adapted to the segmentation using a distance minimization function. Further fine-tuning (e.g., non-rigid registration) may be performed using an iterative closest point method ICP.

The computing unit 2 applies the patient model to the patient-specific set of pose parameters 8 and the patient-specific set of shape parameters 9 in order to calculate an initial surface grid 10 that represents at least the spine and internal organs of the patient 5 in an initial state with the spinal curvature. A target surface grid 11 that represents at least the spine and internal organs of the patient 5 in a target state with a straightened spine is provided.

Providing or creating the target surface grid may be referred to as unposing, which can be understood as deforming the initial surface grid 10 into a reference pose. The reference pose corresponds, for example, to the pose of a template of the patient model (e.g., an average human form of the corresponding patient population without spinal curvature). The aim is to deform the initial surface grid 10 such that the edges of the resulting target surface grid 11 have the same direction vectors as the template.

However, this may lead to the skin and bones not being optimally aligned and/or positioned in relation to each other. Therefore, the deformation may take place under a boundary condition that the distances between the skin and bones remain as constant as possible.

For example, the unposing may be performed by alternating minimizations (1) and (2) in accordance with $$\arg\min\nolimits_{T_{nr},\bar{\theta}_{bo},J_{bo},w_{bo}} \left\| \bar{U}_{bo} - U_{bo} \right\| + \sum_{e \in T_\mu} \left\| T_{bo,e} - T_{\mu,e} \right\| + [\ldots], \quad (1)$$

$$\bar{U}_{bo} = W\!\left(T_{bo}, \bar{\theta}_{bo}, \beta_{bo}; J_{bo}, w_{bo}\right)$$

$$T_{bo} = T_{bo}(\beta_{bo}) + T_{nr}$$

$$\arg\min\nolimits_{\tilde{\theta}_{bo},\bar{\theta}_{bo},J_{bo},w_{bo}} \left\| P\!\left(\tilde{U}_{bo}, T_s\right) - P\!\left(\bar{U}_{bo}, U_s\right) \right\| + [\ldots] \quad (2)$$

$$\tilde{U}_{bo} = W\!\left(T_{bo}, \tilde{\theta}_{bo}\right)$$

$$T_{nr} = \tilde{U}_{bo} - T_{bo}(\beta_{bo})$$

(1) and (2) are optimized alternately, with (1) attempting to adjust the surface grid while (2) attempts to maintain the distance between bone and skin. The results of the optimization (2) (e.g., the optimal values for $\bar{\theta}_{bo}$, $J_{bo}$, $w_{bo}$ and $T_{nr}$) are fed back in (1), and a new optimization according to (1) is performed and so on. $\tilde{\theta}_{bo}$ in (2) may be regarded as very small rotations that deform the template such that the distances between skin (subscript "s") and bones and organs (subscript "bo") are preserved in the deformed and undeformed state. The expressions [ . . . ] represent regularizers that enforce additional boundary conditions, so that $\bar{\theta}_{bo}$, $J_{bo}$, $w_{bo}$ do not differ greatly from their original model values. In addition, a mirror loss may be provided to force the mirroring between the left and right side of the bones.

For Example:

$$T(\beta) = (T_\mu + \beta B),$$

where $T_\mu$ represents the template in the reference pose, which may be deformed according to the shape vectors $\beta$. B are the weighting components determined using principal component analysis. The joint regressor J is a function of $T(\beta)$, and is a learnt parameter. The joint regressor J is a linear regressor that maps the surface grid to 3D key points. The 3D key points are the points at which the deformations of the mesh take place, corresponding, for example, to the knees, ankles, pelvis and so on. It is possible using the linear blend skinning, LBS, function $W(\cdot)$ for a surface grid to be deformed from the reference pose into a new pose. Blend weighting factors w form influence of each pose linearly. This is independent for bones, since all bones may move freely. The weighting factors w are therefore only intended for the organs (e.g., the rotation of the lungs would be a function of a set of thoracic vertebrae).

A much simpler, albeit less exact way of implementing unposing is, for example, to apply the patient model to the patient-specific set of shape parameters 9 and the reference set of pose parameters (e.g., the reference pose) in order to generate the target surface grid 11 directly.

By comparing the target surface grid 11 with the initial surface grid 10, a displacement field is determined for a plurality of vertebrae of the spine of the patient 5. Depending on the displacement field, the support information (e.g., the magnitude 12 and/or direction of the displacement field) is generated and displayed visually.

Optionally, a digitally reconstructed X-ray image 13 may also be generated and displayed based on the target surface grid 11.

As described (e.g., with reference to the figures), the present embodiments enable improved visual support for spinal curvature therapy.

A digital twin of the patient is generated in the form of the initial surface grid in order to create a patient-specific spinal deformation model in the form of the target surface grid. This or the support information may be used for planning the therapy and for support during the therapy for orientation and for monitoring the therapy result.

Independent of the grammatical term usage, individuals with male, female, or other gender identities are included within the term.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for visual support for spinal curvature therapy of a patient, the method comprising:
   providing a patient model for a predetermined patient population for mapping a set of pose parameters and a set of shape parameters onto a three-dimensional surface grid that represents at least a spine and internal organs of the predetermined patient population;
   providing patient image data that shows at least a spine and internal organs of the patient;
   determining, based on the patient image data, a patient-specific set of pose parameters and a patient-specific set of shape parameters;
   calculating an initial surface grid that represents at least the spine and the internal organs of the patient in an initial state with the spine curvature, wherein the calculating of the initial surface grid comprises applying the patient model to the patient-specific set of pose parameters and the patient-specific set of shape parameters;
   providing a target surface grid that represents at least the spine and internal organs of the patient in a target state with a straightened spine;
   determining a displacement field for a plurality of vertebrae of the spine of the patient, the determining of the displacement field for the plurality of vertebrae comprising comparing the target surface grid with the initial surface grid; and
   depending on the displacement field, generating support information and visually displaying the support information.

2. The method of claim 1, wherein the patient image data includes two or more X-ray projection images with different recording directions.

3. The method of claim 1, wherein calculating the initial surface grid comprises:
   calculating a preliminary surface grid, the calculating of the preliminary surface grid comprising applying the patient model to the patient-specific set of pose parameters and the patient-specific set of shape parameters; and
   generating the initial surface grid, the generating of the initial surface grid comprising performing at least one non-rigid registration depending on the preliminary surface grid and the patient image data.

4. The method of claim 3, wherein the patient image data comprises a three-dimensional computed tomography reconstruction.

5. The method of claim 1, wherein providing the target surface grid comprises calculating the target surface grid, calculating the target surface grid comprising applying the patient model to a predetermined reference set of pose parameters and the patient-specific set of shape parameters.

6. The method of claim 3, wherein the non-rigid registration is performed by applying an iterative closest point algorithm.

7. The method of claim 1, wherein the support information includes a magnitude, a direction, or the magnitude and the direction of the displacement field.

8. The method of claim 7, further comprising:
   superimposing a visual representation of the magnitude of the displacement field, a visual representation of the direction of the displacement field, or the visual representation of the magnitude of the displacement field and the visual representation of the direction of the displacement field on the patient image data or a part of the patient image data, or display image data derived from the patient image data; and displaying the superimposition visually.

9. The method of claim 1, further comprising generating a digitally reconstructed X-ray image based on the target surface grid, wherein the support information includes the digitally reconstructed X-ray image.

10. The method of claim 1, wherein the patient model is configured as a skinned multi-person linear model.

11. The method of claim 1, further comprising applying a trained artificial neural network to the patient image data so as to determine the patient-specific set of pose parameters and the patient-specific set of shape parameters.

12. The method of claim 11, wherein determining the patient-specific set of pose parameters and the patient-specific set of shape parameters comprises:

generating at least one feature map, the generating of the at least one feature map comprising applying a feature encoder module of the neural network to the patient image data; and generating the patient-specific set of pose parameters and the patient-specific set of shape parameters, the generating of the patient-specific set of pose parameters and the patient-specific set of shape parameters comprising applying an iterative regression module of the neural network to the at least one feature map.

13. A data processing apparatus comprising:

at least one computing unit configured for visual support for spinal curvature therapy of a patient, the at least one computing unit being configured for visual support for spinal curvature therapy of the patient comprising the at least one computing unit being configured to:

provide a patient model for a predetermined patient population for mapping a set of pose parameters and a set of shape parameters onto a three-dimensional surface grid that represents at least a spine and internal organs of the predetermined patient population;

provide patient image data that shows at least a spine and internal organs of the patient;

determine, based on the patient image data, a patient-specific set of pose parameters and a patient-specific set of shape parameters;

calculate an initial surface grid that represents at least the spine and the internal organs of the patient in an initial state with the spine curvature, wherein the calculation of the initial surface grid comprises application of the patient model to the patient-specific set of pose parameters and the patient-specific set of shape parameters;

provide a target surface grid that represents at least the spine and internal organs of the patient in a target state with a straightened spine;

determine a displacement field for a plurality of vertebrae of the spine of the patient, the determination of the displacement field for the plurality of vertebrae comprising comparison of the target surface grid with the initial surface grid; and depending on the displacement field, generate support information and visually display the support information.

14. An apparatus for visual support for spinal curvature therapy of a patient, the apparatus comprising:

a data processing apparatus comprising:

at least one computing unit configured for visual support for spinal curvature therapy of a patient, the at least one computing unit being configured for visual support for spinal curvature therapy of the patient comprising the at least one computing unit being configured to:

provide a patient model for a predetermined patient population for mapping a set of pose parameters and a set of shape parameters onto a three-dimensional surface grid that represents at least a spine and internal organs of the predetermined patient population;

provide patient image data that shows at least a spine and internal organs of the patient;

determine, based on the patient image data, a patient-specific set of pose parameters and a patient-specific set of shape parameters;

calculate an initial surface grid that represents at least the spine and the internal organs of the patient in an initial state with the spine curvature, wherein the calculation of the initial surface grid comprises application of the patient model to the patient-specific set of pose parameters and the patient-specific set of shape parameters;

provide a target surface grid that represents at least the spine and internal organs of the patient in a target state with a straightened spine;

determine a displacement field for a plurality of vertebrae of the spine of the patient, the determination of the displacement field for the plurality of vertebrae comprising comparison of the target surface grid with the initial surface grid; and depending on the displacement field, generate support information and visually display the support information;

an imaging modality configured to generate the patient image data; and a display device, wherein the at least one computing unit is configured so as to display the support information on the display device.

15. In a non-transitory computer-readable storage medium that stores instructions executable by one or more processors for visual support for spinal curvature therapy of a patient, the instructions comprising:

providing a patient model for a predetermined patient population for mapping a set of pose parameters and a set of shape parameters onto a three-dimensional surface grid that represents at least a spine and internal organs of the predetermined patient population;

providing patient image data that shows at least a spine and internal organs of the patient;

determining, based on the patient image data, a patient-specific set of pose parameters and a patient-specific set of shape parameters;

calculating an initial surface grid that represents at least the spine and the internal organs of the patient in an initial state with the spine curvature, wherein the calculating of the initial surface grid comprises applying the patient model to the patient-specific set of pose parameters and the patient-specific set of shape parameters;

providing a target surface grid that represents at least the spine and internal organs of the patient in a target state with a straightened spine;

determining a displacement field for a plurality of vertebrae of the spine of the patient, the determining of the displacement field for the plurality of vertebrae comprising comparing the target surface grid with the initial surface grid; and depending on the displacement field, generating support information and visually displaying the support information.

16. The non-transitory computer-readable storage medium of claim 15, wherein the patient image data includes two or more X-ray projection images with different recording directions.

17. The non-transitory computer-readable storage medium of claim 15, wherein calculating the initial surface grid comprises:

calculating a preliminary surface grid, the calculating of the preliminary surface grid comprising applying the patient model to the patient-specific set of pose parameters and the patient-specific set of shape parameters; and generating the initial surface grid, the generating of the initial surface grid comprising performing at least one non-rigid registration depending on the preliminary surface grid and the patient image data.

18. The non-transitory computer-readable storage medium of claim 17, wherein the patient image data comprises a three-dimensional computed tomography reconstruction.

\* \* \* \* \*